United States Patent [19]

Carling et al.

[11] Patent Number: 5,376,748
[45] Date of Patent: Dec. 27, 1994

[54] NITROQUINOLONE DERIVATIVES

[75] Inventors: William R. Carling, Bishops Stortford; Julian D. Smith; Paul D. Leeson, both of Cambridge, all of England

[73] Assignee: Merck Sharp & Dohme Limited, Hoddesdon, England

[21] Appl. No.: 1,376

[22] Filed: Jan. 7, 1993

[30] Foreign Application Priority Data

Jan. 15, 1992 [GB] United Kingdom ............... 9200781

[51] Int. Cl.⁵ ............... C07D 401/04; C07D 401/06; C07D 215/18; C07D 215/227
[52] U.S. Cl. ............... 546/158; 546/155; 546/156; 546/157
[58] Field of Search ............... 546/155, 156, 157, 158; 514/312

[56] References Cited

U.S. PATENT DOCUMENTS 3,962,445  6/1976  Buckle et al. ............... 514/312
4,192,876  3/1980  Hardtmann ............... 546/155
4,710,507  12/1987  Campbell et al. ............... 514/312

FOREIGN PATENT DOCUMENTS

0398283A1  11/1990  European Pat. Off. .
0459561A2  12/1991  European Pat. Off. .

OTHER PUBLICATIONS

Carling, Robert W. et al, "3-Nitro-3,4-Dihydro . . . ", J of Medicinal Chemistry, (as yet to be published–due to be published Sep. 1993).
Dingledine, R. et al, "Excitatory Amino . . . ", TiPS, vol. 11, pp. 334–338, Aug. 1990.

Primary Examiner—C. Warren Ivy
Assistant Examiner—D. Margaret M. Mach
Attorney, Agent, or Firm—Robert J. North; Melvin Winokur; Paul D. Matukaitis

[57] ABSTRACT

A class of optionally 4-substituted 3-nitro-2-oxo-1,2,3,4-tetrahydroquinoline derivatives are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA receptor antagonist.

9 Claims, No Drawings

NITROQUINOLONE DERIVATIVES

This invention relates to a class of optionally 4-substituted 3-nitro-2-oxo-1,2,3,4-tetrahydroquinolines which are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivopontocerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293) and anxiolytic (see, for example, Kehne et al., *Eur. J. Pharmacol.*, 1991, 193, 283) effects, and the compounds of the present invention may accordingly be useful in the management of pain and anxiety.

Compounds possessing functional antagonist properties for the NMDA receptor complex are stated in WO-A-91/19493 to be effective in the treatment of mood disorders, including major depression, bipolar disorder, dysthymia and seasonal affective disorder (cf. also Trullas and Skolnick, *Eur. J. Pharmacol.*, 1990, 185, 1). The compounds of the present invention may consequently be of benefit in the treatment and/or prevention of such disorders.

The association of NMDA receptor antagonists with regulation of the dopaminergic system has recently been reported (see, for example, Werling et al., *J. Pharmacol. Exp. Ther.*, 1990, 255, 40; Graham et al., *Life Sciences*, 1990, 47, PL-41; Hutson et al., *Br. J. Pharmacol.*, 1991, 103, 2037; and Turski et al., *Nature* (London), 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Metabolism*, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A-0420806, which are stated to be selective NMDA antaonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

The present invention accordingly provides a compound of formula I, or a salt or prodrug thereof:

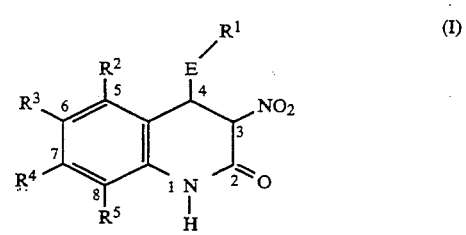

(I)

wherein

E represents a bond or a straight or branched alkylene chain containing from 1 to 4 carbon atoms;

$R^1$ represents hydrogen, $-OR^a$, $-NR^aR^b$, $-CO_2R^a$, $-CONR^1R^b$ or a group of formula

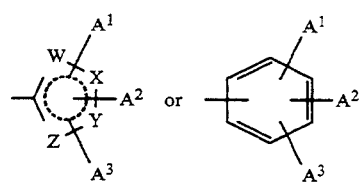

in which the broken circle represents two non-adjacent double bonds in any position in the five-membered ring;

W, X, Y and Z independently represent oxygen, sulphur, nitrogen or carbon, provided that no more than one of W, X, Y and Z represents oxygen or sulphur, at least one of W, X, Y and Z represents carbon and at least one of W, X, Y and Z is other than carbon;

$A^1$, $A^2$ and $A^3$ represent one, two or three substituents (not exceeding the maximum number permissible by the disposition of heteroatoms in the five-membered ring), which substituents are independently selected from hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; or $A^1$ and $A^2$ or $A^2$ and $A^3$ together represent the residue of an aromatic or heteroaromatic ring;

$R^2$, $R^3$, $R^4$ and $R^5$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^1R^b$; or $R^2$ and $R^3$, $R^3$ and $R^4$ or $R^4$ and $R^5$ together represent the residue of an aromatic or heteroaromatic ring; and $R^a$ and $R^b$ independently represent hydrogen, hydrocarbon or a heterocyclic group.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl and t-butyl.

Suitable alkenyl groups include straightchained and branched alkenyl groups containing from 2 to 6 carbon atoms. Typical examples include vinyl and allyl groups.

Suitable alkynyl groups include straightchained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

Particular aryl($C_{1-6}$)alkyl groups include benzyl, phenethyl, phenylpropyl and phenylbutyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, pyrrolyl, indolyl, imidazolyl, oxadiazolyl and thiadiazolyl groups. Particular heteroaryl groups are pyridyl, furyl, benzofuryl, thienyl, benzthienyl, pyrrolyl, indolyl and oxadiazolyl.

Particular heteroaryl($C_{1-6}$)alkyl groups include indolylethyl, indolylpropyl and thienylethyl.

The hydrocarbon and heterocyclic groups may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, $C_{1-6}$ alkoxy($C_{1-6}$)alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, arylthio, amino, mono- or di($C_{1-6}$)alkylamino, $C_{2-6}$ alkylcarbonylamino, $C_{2-6}$ alkoxycarbonylamino and $C_{2-6}$ alkoxycarbonylamino($C_{1-6}$)alkyl.

The term "halogen" as used herein includes fluorine, chlorine, bromine and iodine, especially chlorine.

The alkylene chain E may be, for example, methylene, ethylene, 1-methylethylene, propylene or 2methylpropylene, preferably methylene. Alternatively, the group E may represent a single bond such that the moiety $R^1$ in formula I is attached directly to the tetrahydroquinoline ring system.

The five-membered heteroaromatic ring containing the ring atoms W to Z may be, for example, a furan, thiophene, pyrrole, oxazole, thiazole, isoxazole, isothiazole, oxadiazole or thiadiazole ring, in particular a furan, thiophene, pyrrole, 1,2,4-oxadiazole, 1,3,4-oxadiazole, 1,2,4-thiadiazole or 1,3,4-thiadiazole ring. Preferably the ring is a furan, thiophene, pyrrole, 1,2,4-oxadiazole or 1,2,4-thiadiazole ring.

The number of substituents $A^1$, $A^2$ and/or $A^3$ present on the five-membered heteroaromatic ring containing the ring atoms W to Z is one, two or three depending upon the disposition of heteroatoms in the heteroaromatic ring. Thus where, for example, the five-membered heteroaromatic ring is an oxadiazole or thiadiazole ring, only one substituent will be permitted; where, for example, the five-membered heteroaromatic ring is an oxazole or thiazole ring, one or two substituents will be permitted; and where, for example, the fivemembered heteroaromatic ring is a furan, thiophene or pyrrole ring, one, two or three substituents will be permitted.

Suitable values for the groups $A^1$ $A^2$ and/or $A^3$ include hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, optionally substituted aryl, optionally substituted aryl($C_{1-6}$)alkyl, halogen, cyano, trifluoromethyl, nitro, $C_{1-6}$ alkoxy, $C_{2-6}$ alkenyloxy, $C_{1-6}$ alkylthio, $C_{2-6}$ alkenylthio, $-COR^a$ or $-NR^aR^b$, in which $R^a$ and $R^b$ are as defined above.

When $R^1$ in the compounds of formula I above represents a group of formula $-OR^a$, $-NR^aR^b$, $-CO_2R^a$ or $-CONR^1R^b$, the substituents $R^a$ and $R^b$ are suitably selected independently from hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl($C_{1-6}$)alkyl, heteroaryl and heteroaryl($C_{1-6}$)alkyl, any of which groups may be optionally substituted.

Representative values of $R^1$ include hydrogen, methoxy, dimethylamino, methoxycarbonyl, ethoxycarbonyl, methylaminocarbonyl, phenylaminocarbonyl, benzylaminocarbonyl, dimethyl-aminocarbonyl, N-methyl-N-phenylaminocarbonyl and methyloxadiazolyl.

In a particularly preferred embodiment of the present invention, E represents a bond and $R^1$ represents hydrogen.

The benzo moiety of the tetrahydroquinoline ring system shown in formula I above preferably contains at least one non-hydrogen substituent. Particular substituents include halogen, cyano, trifluoromethyl, nitro, hydroxy, amino, carboxy, $C_{1-6}$ alkyl, $C_{1-6}$ alkoxy, $C_{1-6}$ alkylthio and $C_{2-6}$ alkoxycarbonyl. Suitably, $R^5$ represents hydrogen and $R^2$, $R^3$ and $R^4$ independently represent hydrogen, halogen, nitro, amino or $C_{1-6}$ alkyl, provided that at least one of $R^2$, $R^3$ and $R^4$ is other than hydrogen. Preferably, $R^3$ and $R^5$ each represents hydrogen and $R^2$ and $R^4$ independently represent hydrogen, nitro, amino, methyl or halogen, especially chlorine, provided that at least one of $R^2$ and $R^4$ is other than hydrogen. In a preferred embodiment, $R^4$ represents chlorine.

Where $R^2$ and $R^3$, $R^3$ and $R^4$, $R^4$ and $R^5$, $A^1$ and $A^2$ or $A^2$ and $A^3$ represent the residue of an aromatic or heteroaromatic ring, this is suitably an optionally substituted benzene, pyridine, thiophene, thiazole or thiadiazole ring. As optional substituents on the aromatic or heteroaromatic ring may be mentioned nitro, and $C_{1-6}$ alkoxy such as methoxy.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of formula I above include alkali metal salts, e.g. sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA, and salts and prodrugs thereof:

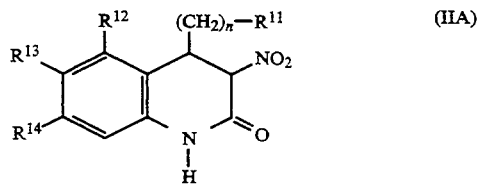

(IIA)

wherein n is zero, 1, 2 or 3, preferably zero or 1;

$R^{11}$ represents hydrogen, $-OR^{16}$, $-NR^{16}R^{17}$, $-CO_2R^{16}$ or $-CONR^{16}R^{17}$;

$R^{12}$, $R^{13}$ and $R^{14}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl; and $R^{16}$ and $R^{17}$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl or heteroaryl($C_{1-6}$)alkyl, any of which groups may be optionally substituted.

Examples of optional subtituents on the groups $R^{16}$ and/or $R^{17}$ suitably include hydroxy, $C_{1-6}$ alkoxy, $C_{1-6}$ alkoxy($C_{1-6}$)alkoxy and $C_{2-6}$ alkoxycarbonylamino($C_{1-6}$)alkyl, especially hydroxy, methoxy, methoxymethoxy and t-butoxycarbonylaminomethyl.

Particular values of $R^{11}$ with respect to formula IIA include hydrogen, methoxy, dimethylamino, methoxycarbonyl, ethoxycarbonyl, methylaminocarbonyl, phenylaminocarbonyl, benzylaminocarbonyl, dimethylaminocarbonyl and N-methyl-N-phenylaminocarbonyl.

In a preferred embodiment, n is zero and $R^{11}$ is hydrogen. When $R^{11}$ is other than hydrogen, n is suitably other than zero and preferably 1.

Suitably, $R^{12}$, $R^{13}$ and $R^{14}$ are independently selected from hydrogen, halogen, nitro, amino and $C_{1-6}$ alkyl. Ideally, at least one of $R^{12}$, $R^{13}$ and $R^{14}$ is other than hydrogen. Preferably, $R^{13}$ represents hydrogen, one of $R^{12}$ and $R^{14}$ represents halogen or nitro, and the other of $R^{12}$ and $R^{14}$ represents hydrogen, halogen or nitro. In a particular embodiment, $R^{12}$ and $R^{13}$ each represents hydrogen and $R^{14}$ represents halogen, especially chlorine.

Another sub-class of compounds according to the invention is represented by the compounds of formula IIB, and salts and prodrugs thereof:

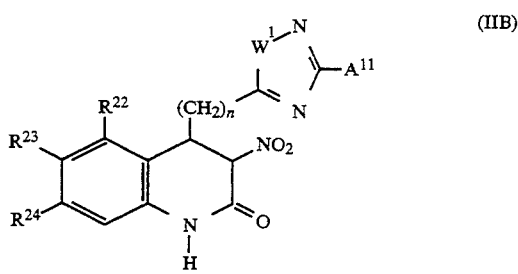

(IIB)

wherein n is zero, 1, 2 or 3, preferably 1;

$W^1$ represents oxygen or sulphur, preferably oxygen;

$A^{11}$ represents hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio, $C_{2-6}$ alkylcarbonyl, arylcarbonyl or $C_{2-6}$ alkoxycarbonyl; and $R^{22}$, $R^{23}$ and $R^{24}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl.

Examples of suitable values for the group $A^{11}$ include hydrogen, halogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio and arylcarbonyl. Particular values of $A^{11}$ include hydrogen, bromo, methyl, ethyl, isopropyl, vinyl, allyl, cyclopropyl, cyclopropylmethyl, phenyl, benzyl, allyloxy, allylthio and benzoyl, especially methyl.

Suitably, $R^{22}$, $R^{23}$ and $R^{24}$ are independently selected from hydrogen, halogen, nitro, amino and $C_{1-6}$ alkyl. Ideally, at least one of $R^{22}$, $R^{23}$ and $R^{24}$ is other than hydrogen. Preferably, $R^{23}$ represents hydrogen, one of $R^{22}$ and $R^{24}$ represents halogen or nitro, and the other of $R^{22}$ and $R^{24}$ represents hydrogen, halogen or nitro. In a particular embodiment, $R^{22}$ and $R^{23}$ each represents hydrogen and $R^{24}$ represents halogen, especially chlorine.

Specific compounds within the scope of the present invention include:

7-chloro-3-nitro-2-oxo-1,2,3,4-tetrahydroquinoline;
4-methoxycarbonylmethyl-3-nitro-2-oxo-1,2,3,4-tetrahydroquinoline;
7-chloro-4-methoxycarbonylmethyl-3-nitro-2-oxo-1,2,3,4-tetrahydroquinoline;
7-chloro-4-ethoxycarbonylmethyl-3-nitro-2-oxo-1,2,3,4-tetrahydroquinoline;
7-chloro-4-methylaminocarbonylmethyl-3-nitro-2-oxo-1,2,3,4-tetrahydroquinoline;
7-chloro-3-nitro-2-oxo-4-phenylaminocarbonylmethyl-1,2,3,4-tetrahydroquinoline;
4-benzylaminocarbonylmethyl-7-chloro-3-nitro-2-oxo-1,2,3,4-tetrahydroquinoline;
7-chloro-4-(N,N-dimethylaminocarbonylmethyl)-3-nitro-2-oxo-1,2,3,4-tetrahydroquinoline;
7-chloro-4-(N-methyl-N-phenylaminocarbonylmethyl)-3-nitro-2-oxo-1,2,3,4-tetrahydroquinoline;
7-chloro-4-(3-methyl-1,2,4-oxadiazol-5-ylmethyl)-3-nitro-2-oxo-1,2,3,4-tetrahydroquinoline;
and salts and prodrugs thereof.

The present invention also provides pharmaceutical compositions comprising at least one of the novel compounds according to the invention in association with a pharmaceutically acceptable carrier.

The pharmaceutical compositions of this invention are preferably in unit dosage forms such as tablets, pills, capsules, powders, granules, sterile parenteral solutions or suspensions, or suppositories, for oral, parenteral or rectal administration. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises the cyclisation of a compound of formula III:

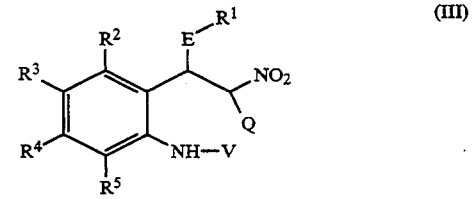

(III)

wherein $R^1$, $R^2$, $R^3$, $R^4$, $R^5$ and E are as defined above, Q represents a reactive carboxylate moiety, and V represents hydrogen or an amino-protecting group; accompanied, where necessary, by removal of the amino-protecting group V.

Suitable values for the reactive carboxylate moiety Q include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group Q represents methoxycarbonyl or ethoxycarbonyl.

Suitable examples of amino-protecting groups for the substituent V include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, trityl, o-nitrophenylsulphenyl or benzylidene.

A preferred amino-protecting group is acetyl.

The removal of the amino-protecting group present in the resultant compound may be effected by an appropriate procedure known from the art, depending upon the nature of the protecting group employed.

The cyclisation of the compound of formula III is advantageously effected under conditions which afford concomitant removal of the nitrogen-protecting group V, if present. For example, where V represents acetyl and Q is an ethoxycarbonyl group, the reaction is conveniently carried out in methanolic hydrochloric acid at the reflux temperature of the solvent.

The intermediates of formula III above may conveniently be prepared by reacting a compound of formula Q—CH$_2$—NO$_2$ with a compound of formula IV:

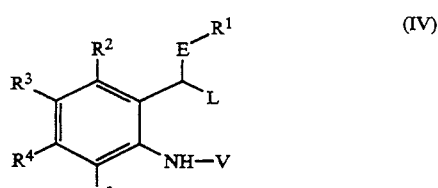

wherein $R^1$, $R^2$, $R^3$, $R^4$, $R^5$, E, Q and V are as defined above, and L represents a leaving group; in the presence of a strong base.

The leaving group L is suitably a halogen atom, e.g. chlorine.

Where, for example, the reagent of formula Q—CH$_2$—NO$_2$ is ethyl nitroacetate, the strong base employed will advantageously be sodium ethoxide and the reaction will conveniently be carried out in N,N-dimethylformamide at a temperature in the region of 60° C. Alternatively, where appropriate, the sodium salt of the reagent of formula Q—CH$_2$—NO$_2$ may advantageously be prepared prior to commencement of the reaction and stored until required.

A typical procedure for the preparation of the intermediates of formula IV is illustrated by the following scheme:

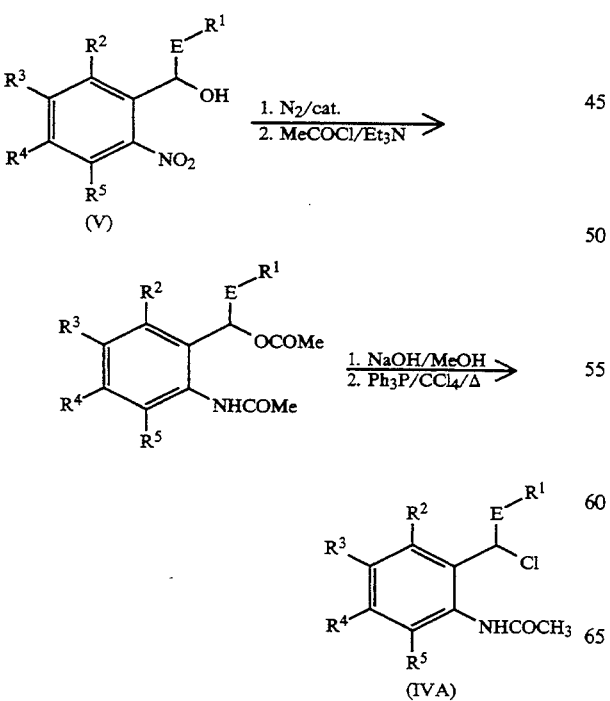

wherein $R^1$, $R^2$, $R^3$, $R^4$, $R^5$, E, Q and V are as defined above.

In an alternative process, the compounds according to the invention in which E is a methylene group and the substituent $R^1$ is an electron-withdrawing group may be prepared by intramolecular Michael cyclisation of a compound of formula VI:

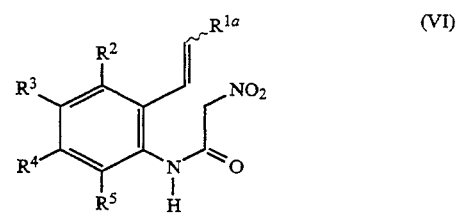

wherein $R^2$, $R^3$, $R^4$ and $R^5$ are as defined above and $R^{1a}$ is an electron-withdrawing group corresponding to the substituent $R^1$ as defined above.

The electron-withdrawing substituent $R^{1a}$ suitably represents a group of formula —CO$_2R^a$ or —CONR$^1R^b$, wherein $R^a$ and $R^b$ are as defined above, or a five-membered heteroaromatic ring containing the ring atoms W and Z as defined above, provided that the heteroaromatic ring in question has electron-withdrawing properties. A heteroaromatic ring of particular note in this regard is the optionally 3-substituted 1,2,4-oxadiazol-5-yl ring.

The cyclisation of the compound of formula VI is suitably effected in the presence of a strong base such as a sodium alkoxide, e.g. sodium methoxide, ideally in the corresponding alkanol, e.g. methanol.

The intermediates of formula VI above may conveniently be prepared from the corresponding aniline derivatives of formula VII:

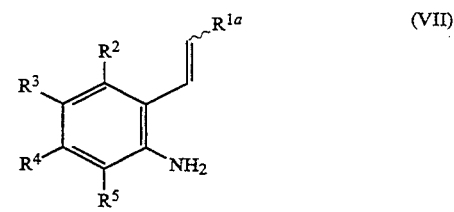

wherein $R^2$, $R^3$, $R^4$, $R^5$ and $R^{1a}$ are as defined above; by treatment with phosgene in the presence of triethylamine, followed by treatment of the product thereby obtained with nitromethane in the presence of a strong base such as potassium t-butoxide.

Both steps of the above procedure are suitably carried out in tetrahydrofuran as solvent, conveniently at a temperature in the region of 0° C.

The intermediates of formula VII above may conveniently be prepared by reduction of the corresponding nitro compounds of formula VIII:

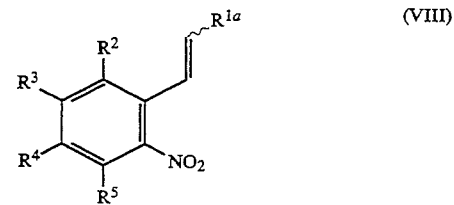

wherein $R^2$, $R^3$, $R^4$, $R^5$ and $R^{1a}$ are as defined above.

A suitable reducing agent is zinc/acetic acid in ethanol.

Where appropriate, the desired intermediate of formula VII or VIII may be obtained from a precursor compound of formula VII or VIII respectively by suitable functional group interconversion. For example, a compound of formula VIII wherein $R^{1a}$ represents a group of formula —$CONR^1R^b$ may be prepared from a compound of formula VIII wherein $R^{1a}$ represents —$CO_2R^a$ by saponification followed by condensation with an appropriate amine H—$NR^aR^b$. Similarly, a compound of formula VII wherein $R^{1a}$ represents an optionally 3substituted 1,2,4-oxadiazol-5-yl substituent may be prepared by reacting a compound of formula VII wherein $R^{1a}$ represents 2 with a compound of formula —CO $R^aA^1$—C(=NOH)$NH_2$ in the presence of sodium hydride, in a suitable solvent such as tetrahydrofuran.

The compounds of formula VIII wherein $R^{1a}$ represents a group of formula —$CO_2R^a$ may be prepared by Wittig reaction between a reagent of formula $Ph_3P=CHCO_2R^a$ and an aldehyde of formula IX:

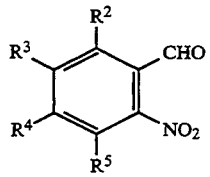

(IX)

wherein $R^2$, $R^3$, $R^4$, $R^5$ and $R^a$ are as defined above.

The Wittig reaction is conveniently effected by heating the reagents together at reflux temperature in a solvent such as toluene.

Where they are not commercially available, the intermediates of formulae V and IX above may be prepared by methods analogous to those described in the accompanying Examples, or by procedures well known from the art.

It will be appreciated that any compound of formula I initially obtained from any of the above processes may, where appropriate, subsequently be elaborated into a further desired compound of formula I, for example by methods analogous to those described above for the intermediates of formula VIII.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA or AMPA concentration-response curves produced by the compound under test. Of those compounds of the accompanying Examples which were tested, all were found to possess a $K_b$ value in response to NMDA of below 150 μM. The compound of Example 2 was tested and was found to possess a $K_b$ value in response to AMPA of below 150 μM.

Binding Studies

The ability of test compounds to displace either $^3$H-glycine binding or $^3$H-L-689,560 (trans-2-carboxy -5,7-dichloro-4-phenylaminocarbonylamino-1,2,3,4-tetrahydroquinoline) binding to the strychnine-insensitive site present on the NMDA receptor of rat forebrain membranes was determined. $^3$H-Glycine binding was measured by the method of Donald et al., *Proceedings of The British Pharmacological Society*, University of Nottingham, September, 1988, Abstract P122. $^3$H-L-689,560 binding was measured by the method of Grimwood et al., *Proceedings of the British Pharmacological Society*, July, 1991, Abstract C78. The concentration of the compounds of the accompanying Examples required to displace 50% of the specific binding of either tritiated ligand ($IC_{50}$) is below 50 μM in each case.

EXAMPLE 1

7-Chloro-4-methoxycarbonylmethyl-3-nitro-3,4-dihydroquinolin-2-one a) Trans-4-Chloro-2-nitro-1-(2-methoxycarbonylethenyl)-benzene 4-Chloro-2-nitrobenzaldehyde (5 g, 0.027M) was dissolved in toluene (150 ml) with methyl (triphenylphosphoranylidene) acetate (9.91 g, 1.1 molar equivalents) and heated under reflux for 1h. The reaction mixture was concentrated under vacuum and the residue was purified by chromatography on silica gel using dichloromethane as eluent to give the required compound (6.4 g, 98%) as a solid. δ(360MHz, $CDCl_3$) 3.83 (3H, s, $CH_3$), 6.36 (1H, d, J=15.9Hz, $CH_A$=$CH_B$), 7.58 (1H, d, J=8.4Hz, 6H), 7.63 (1H, dd, J=8.4 and 2.0Hz, 5-H), 8.04 (1H, d, J=2.0Hz, 3-H), 8.05 (1H, d, J=8.4Hz, $CH_A$=$CH_B$); MS (EI) m/e 241 [M+].

b) Trans-2-Amino-4-chloro-1-(2-methoxycarbonylethenyl)benzene

The product from Example 1a (2 g, 0.0083M) was dissolved in glacial acetic acid (20 ml) and absolute ethanol (20 ml) then zinc dust (2 g) was added and the reaction mixture was heated at 60° C. for 4h under an atmosphere of nitrogen. After cooling, the mixture was filtered and the solution was concentrated under vacuum. The residue was dissolved in ethyl acetate (200 ml) and washed with dilute sodium hydroxide solution, then dried ($Na_2SO_4$), filtered and concentrated in vacuo. Purification of the residue on silica gel, using 20% ethyl acetate in hexane as the eluent, gave the required compound as a yellow solid (1.25 g, 71%). δ360MHz, $CDCl_3$) 3.80 (3H, s, $CH_3$), 4.02 (2H, br s, $NH_2$), 6.32 (1H, d, J=15.8Hz, $CH_A$=$CH_B$), 6.70 (1H, d, J=1.9Hz, H-3), 6.73 (1H, dd, J=8.3 and 1.9Hz, 5-H), 7.28 (1H, d, J =8.3Hz, 6-H), 7.72 (1H, d, J=15.8Hz, $CH_A$=$CH_B$); MS (EI) m/e 211[M+].

c) Trans-4-Chloro-2-nitromethylcarbonylamino-1-methoxycarbonyl ethenyl-benzene

The product from Example 1b (1g, 0.00473M) was dissolved in dry tetrahydrofuran (100 ml) with triethylamine (1.38 ml, 0.0099M) cooled to 0° C. and phosgene (3.1 ml of a 1.93 molar solution in toluene, 0.006M) was added. After stirring at 0° C. for 20 minutes a preformed solution of nitromethane arion (nitromethane (1.3 ml, 0.024M) in tetrahydrofuran (80 ml) at 0° C. with 26 ml of 1 molar potassium tertiary butoxide solution in tetrahydrofuran) was added by cannula. After stirring at 0° C. for 1h, the reaction mixture was poured into ice-cold hydrochloric acid and extracted into diethyl ether (3×100 ml). The combined organic layers were dried ($Na_2SO_4$), filtered and concentrated in vacuo and the residue was purified by trituration with diethyl ether to give the required compound as a white solid (0.56 g, 40%); 8 (360MHz, DMSO) 3.74 (3H, s, $CH_3$), 5.63 (2H, s, $CH_2NO_2$), 6.66 (1H, d, J=15.8Hz, $CH_A$=$CH_B$), 7.36 (1H, dd, J=8.6 and 1.9Hz, 5-H), 7.65 (1H, d, J=1.9Hz, 3-H), 7.79 (1H, d, J=15.8Hz, $CH_A$=$CH_B$), 7.89 (1H, d, J=8.6Hz, 6-H); MS (EI) m/e 298 [M+].

d) 7-Chloro-4-methoxycarbonylmethyl-3-nitro-3,4-dihydroquinolin-2-one

The product from Example 1c (0.54 g, 0.00181M) was dissolved in dry methanol (100 ml) and sodium methoxide (generated by dissolving 80% sodium hydride (0.163 g, 3 molar equivalents) in dry methanol (30 ml)) was added. The reaction mixture was stirred at room temperature for 14h then methanol that had been saturated with hydrogen chloride (100 ml) was added and the solvents were removed under vacuum. The residue was dissolved in ethyl acetate (100 ml) and extracted with saturated potassium carbonate solution (2×100 ml). The combined aqueous layers were washed with diethyl ether (2×100 ml) then acidified to pHI with concentrated hydrochloric acid and extracted into ethyl acetate (2×100 ml), dried ($Na_2SO_4$), filtered and concentrated in vacuo. The residue obtained was triturated with diethyl ether and collected by filtration to give the title compound as a white solid; m.p.=135° C. (0.077 g, 14%); 8 (360MHz, DMSO) (9.2:1 mixture of epimers) 2.64 (1H, dd, J=16.6 and 7.4Hz, $CH_AH_BCH_C$), 2.86 (1H, dd, J=16.6 and 5.5Hz, $CH_AH_BCH_C$), 3.60 (3H, s, $CH_3$, major epimer), 3.63 (3H, s, $CH_3$, minor epimer), 4.12 (1H, m, $CH_ACH_BCH_C$), 5.78 (1H, d, J=6.2Hz, $CHNO_2$, major epimer), 5.87 (1H, d, J=5.0Hz, $CHNO_2$, minor epimer), 6.98 (1H, d, J=1.9Hz, 8-H), 7.09 (1H, dd, J=8.6 and 1.9Hz, 6-H), 7.19 (1H, d, J =8.6Hz, minor epimer), 7.26 (1H, d, J=8.6Hz, 5-H, major epimer); MS (EI) m/e 298 [M+]. Found: C, 48.10; H, 3.79; N, 9.16. $C_{12}H_{11}ClN_2O_5$ requires C, 48.26; H, 3.71; N, 9.38%.

EXAMPLE 2

7-Chloro-3-nitro-3,4-dihydroquinolin-2-one a) 5-Chloro-2-hydroxymethyl-acetanilide 4-Chloro-2-nitrobenzyl alcohol (25.42 g, 0.136M) was dissolved in methanol (1000 ml) then 5% platinum sulphide on carbon catalyst (2 g) was added and the reaction mixture was shaken under a 50 p.s.i. atmosphere of hydrogen for 18h. The mixture was filtered, concentrated under vacuum then redissolved in dichloromethane (1000 ml) with triethylamine (41.8 ml, 0.3M) and cooled to 0° C. Acetyl chloride (21.3 ml, 0.3M) was added dropwise then the reaction mixture was stirred at room temperature for 14h. The solution was washed with 1N HCl (2×500 ml) and brine (1×500 ml) then dried ($MgSO_4$), filtered and concentrated in vacuo. The residue was dissolved in methanol (500 ml) and a solution of sodium hydroxide (6 g, 0.15M) in water (200 ml) was added. After stirring at room temperature for 1h, the methanol was removed in vacuo and the aqueous residue was extracted with ethyl acetate (3×300 ml). The combined organic layers were washed with saturated sodium hydrogen carbonate solution (1×200 ml), then brine (1×200 ml), dried ($MgSO_4$), filtered and evaporated to give the required compound (24.41 g, 90%); δ360MHz, DMSO) 2.07 (3H, s, $CH_3$), 4.48 (2H, d, J=5.5Hz, $CH_2OH$), 5.36 (1H, t, J=5.5Hz, $CH_2OH$), 7.18 (1H, dd, J=8.5 and 1.9Hz, 4-H), 7.40 (1H, d, J=8.5Hz, 3-H), 7.68 (1H, d, J=1.9Hz, 6-H), 9.34 (1H, br s, NH).

b) 2-Chloromethyl-5-chloro-acetanilide

The product from Example 2a (2 g, 0.01M) and triphenylphosphine (2.62 g, 0.01M) were dissolved in carbontetrachloride (50 ml) and tetrahydrofuran (50 ml) and heated at reflux, under nitrogen, for 2h. The solvents were removed under vacuum and the residue was purified by silica gel chromatography using 20-40% ethyl acetate in hexane as eluent to give the required product (1.16 g, 53%) m.p.=148–154° C. dec; δ360MHz, DMSO) 2.10 (3H, s, $CH_3$), 4.83 (2H, s, $CH_2$), 7.23 (1H, dd, J=8.5 and 2.0Hz, 4-H), 7.48 (1H, d, J=8.5Hz, 3-H), 7.68 (1H, d, J=2.0Hz, 6-H), 9.56 (1H, br s, NH); MS (EI) m/e 217 [M+].

c) 5-Chloro-2-((2/-ethoxycarbonyl)2/-nitro)ethyl acetanilide

The product from Example 2b (0.55 g, 0.0025M) and the sodium salt of ethylnitroacetate (1.18 g, 0.0076M) were dissolved in dry dimethylformamide and heated at 60° C. under nitrogen for 1h. The reaction mixture was poured into dilute hydrochloric acid (200 ml) and extracted into ethyl acetate (2×150 ml). The combined organic layers were washed with water (1×200 ml) and brine (1×200 ml) then dried ($MgSO_4$), filtered and concentrated in vacuo to give a brown oil. This was purified by chromatography on silica gel using 30–50% ethyl acetate in hexane as eluent to give the required product as a white solid (0.296 g, 38%) δ(360MHz, DMSO) 1.16 (3H, t, J=7.1Hz, $CH_3CH_2O$), 2.07 (3H, s, J=$CH_3CONH$), 3.48 (2H, m, $CH_AH_BCH_C$), 4.19 (2H, q, J=7Hz, $CH_3CH_2O$), 5.83 (1H, dd, J =8.8 and 6.6Hz, $CH_AH_BCH_C$), 7.22 (2H, m, 3-H and 4-H), 7.53 (1H, d, J=1.9Hz, 6-H), 9.54 (1H, br s, NH); MS (EI) m/e 314 [M+].

d) 7-Chloro-3-nitro-3,4-dihydroquinolin-2-one

The product from Example 2c (0.25 g, 0.0008M) was dissolved in methanol (10 ml) that had been presaturated with hydrogen chloride and heated under reflux for 1h then concentrated under vacuum. The residue was recrystallised from ethyl acetate/hexane to give the required compound as a white solid (0.083 g, 46%) m.p.=194–197° C.; δ(360MHz, DMSO) 3.58 (2H, m, CH$_A$H$_B$CH$_C$NO$_2$), 5.87 (1H, dd, JJ=10.0 and 6.8Hz, CH$_A$H$_B$CH$_C$NO$_2$), 6.94 (1H, d, J=1.9Hz, H=8), 7.07 (1H, dd, J=8.1 and 1.8Hz, 6-H), 7.29 (1H, d, J=8.1Hz, 5-H), 0.99 (1H, br s, NH); MS (EI) m/e 226 [M+]; Found: C, 48.05; H, 2.99; N, 11.85. C$_9$H$_7$ClN$_2$O$_3$ requires C, 47.77; H, 3.18; N, 2.22%.

EXAMPLE 3

7-Chloro-4-[(N-methyl)phenylaminocarbonyl]methyl-3-nitro-3,4-dihydroquinolin-2-one. Sodium salt.

a. Cis and trans-4-chloro-2-nitro-1-(2-carboxy ethenyl)benzene.

4-Chloro-2-nitrobenzaldehyde (5 g, 0.027m) was dissolved in toluene (150 ml) with methyl (triphenylphosphoranylidene) acetate (9.91 g, 1.1 molar equivalents) and heated under reflux for 1h. The reaction mixture was concentrated under vacuum and the residue was purified by chromatography on silica gel using dichloromethane as eluent to give a solid (Example 1a). This was dissolved in 50% aqueous acetone (500 ml) with sodium hydroxide (3.5 g) and the solution was stirred at room temperature for 2h. The acetone was removed under vacuum and the aqueous residue was acidified to pH 1 using concentrated HCl then extracted with ethyl acetate, dried (Na$_2$SO$_4$)), filtered and concentrated in vacuo to give the required product (5.5 g, 90%). m.p.=165° C. (sub); δ(250MHz, CDCl) 6.15 (1H, d, J=11.9Hz, cis CH$_A$=CH$_B$), 6.35 (1H, d, J=15.7Hz, trans (CH$_A$=CH$_B$), 7.45 (1H, d, J=11.9Hz, cis CH$_A$=CH$_B$), 7.34–7.64(4H, m cis 5-H and 6-H, trans 5-H and 6-H), 8.06 (1H, d, J=2.0Hz, H-3), 8.17 (1H, d, J=2.0Hz, H-3), 8.13 (1H, d, J=15.7Hz, trans CH$_A$=CH$_B$); MS (EI) m/e 227 [M+].

b. Trans-4-chloro-2-nitro-2-(2-[(N-(methyl)-phenylaminocarbonyl]ethenyl)benzene

The product from Example 3a (5 g, 0.022m) was dissolved in tetrahydrofuran (200 ml) with triethylamine (9.1m, 3 molar equivalents), 1-hydroxybenzotriazole (4.46 g, 1.5 molar equivalents ) and 1-( 3-dimethylaminopropyl )-3-ethylcarbodiimide hydrochloride (6.5 g, 1.5 molar equivalents) and stirred at room temperature for 14h. The solvent was evaporated under vacuum and the residue was dissolved in ethyl acetate (500 ml) and washed with 0.5 N citric acid solution (3×200 ml), saturated sodium hydrogen carbonate solution (3×200 ml) and brine (1×200 ml). The organic layer was dried (Na$_2$SO$_4$), filtered and concentrated under vacuum to give a residue which was purified by silica gel chromatography using 30% ethyl acetate in hexane as eluent to give the required product as a white solid (3.97 g, 57%). m.p.=99°–101° C.; δ(360MHz, DMSO) 3.32 (3H, s, N-CH$_3$), 6.39 (1H, d, J=15.9Hz), 7.14:7.82 (8H, m, H-5, H-6 and Ph), 8.12 (1H, d, J=1.9Hz, 3-H); MS EI m/e 316 [M+].

c. Trans-2-amino-4-chloro-1-(2-[(N-methyl) phenylaminocarbonyl]ethenyl)benzene

The product from Example 3b (3.9 g, 0.0123m) was dissolved in ethanol (40 ml) with glacial acetic acid (40 ml) and zinc dust (5 g) was added. The reaction mixture was heated at 60° C. for 3h then filtered and the solvents removed under vacuum. The residue was in hexane as eluent to give the required product as a yellow oil (2.18 g, 54%). δ(360MHz, DMSO) 3.30 (3H, s, NCH$_3$), 5.71 (2H, br, s, NH$_2$), 6.19 (1H, d, JJ=15.7Hz, CH$_A$=CH$_B$), 6.44 (1H, dd, J=8.4 and 2.0Hz, 5-H), 6.69 (1H, d, J=2.0Hz, 3-H), 6.93 (1H, d, J=8.4Hz, 6-H), 7.30–7.49 (5H, m, Ph), 7.64 (1H, d, J=15.7Hz, CH$_A$=CH$_B$); MS (EI) m/e 286 [M+].

d. 7-Chloro-4-[(N-methyl)phenylaminocarbonyl]-methyl-3-nitro-3,4-dihydroquinolin-2-one. Sodium salt.

Treatment of the product from Example 3c under the conditions described in Examples 1c and 1d gave the title compound which was isolated as its sodium salt by dissolution in a solution of sodium methoxide in methanol, concentration to a small volume and collection by filtration. m.p.=240° C. (dec). δ(360MHz, D$_2$O) 2.48 (1H, dd, J=13.4 and 5.2Hz, CH$_A$H$_B$CH$_C$), 2.52 (1H, dd, J=13.4 and 8.6Hz, CH$_A$CH$_B$CH$_C$), 3.13 (3H, s, CH$_3$), 4.66 (1H, dd, J=8.6 and 5.2Hz, CH$_A$CH$_B$CH$_C$), 6.74 (2H, m, aromatics), 6.88 (1H, d, J=1.8Hz, 8-H), 7.02 (1H, d, J=8.2Hz, 5-H), 7.06 (1H, dd, J=8.2 and 1.8Hz, 6-H), 7.36 (3H, m, aromatics); MS (FAB m/e 396 [MH]+; Found C, 51.67; H, 3.95, N, 9.84. C$_{18}$H$_{15}$ClN$_3$O$_4$Na. 1.2H$_2$O requires C, 51.80; H, 4.20; N, 10.07%.

EXAMPLE 4

7:Chloro-4(N,N-dimethylaminocarbonyl)methyl-3-nitro-3,4-dihydroquionolin-2-one

The title compound as prepared as for Example 3, parts a, b (using dimethylamine hydrochloride in place of N-methylaniline), and c; and Example 1, parts c and d, to yield the crude product which was recrystallised from ethyl acetate hexane to give a white solid. m.p.=210°–211° C. (decomp). Found: C, 50.17; H, 4.57; N, 13.08%. C$_{13}$H$_{14}$ClN$_3$O$_4$ requires C, 50.09; H, 4.53; N, 13.48%. δ(360MHz, DMSO) (11:1 mixture of epimers) 2.69 (1H, dd, J=16.6 and 7.4Hz, CH$_A$H$_B$CH$_C$) 2.77–2.85 (7H, m, CH$_A$CH$_B$CH$_C$, N(CH$_3$)$_2$), 4.14 (1H, m, CH$_A$H$_B$CH$_C$) 5.74 (1H, d, J=6.2Hz, CHNO$_2$ major epimer, 5.80 (1H, d, J=5.0Hz, CHNO$_2$ minor epimer), 6.97 (1H, d, J=1.9Hz, 8-H), 7.07 (1H, dd, J=8.6 and 1.9Hz, 6oH), 7.20 (1H, m, 5-H); MS (CI+) m/e 312 [M+H].

EXAMPLE 5

Tablet Preparation

Tablets containing 1.0, 2.0, 25.0, 26.0, 50.0 and 100.0mg, respectively of the following compounds are prepared as illustrated below:

7-Chloro-4-methoxycarbonylmethyl-3-nitro-3,4-dihydroquinolin-2-one

7-Chloro-3-nitro-3,4-dihydroquinolin-2-one

7-Chloro-4-[(N-methyl)phenylaminocarbonyl]methyl-3-nitro-3,4-dihydroquinolin-2-one. Sodium salt.

7-Chloro-4(N,N-dimethylaminocarbonyl)methyl-3-nitro-3,4-dihydroquinolin-2-one

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0mg, 2.0mg, 25.0mg, 26.0mg, 50.0mg and 100mg of the active ingredient per tablet.

What is claimed is:

1. A compound of formula I, or a pharmaceutically acceptable salt or prodrug thereof:

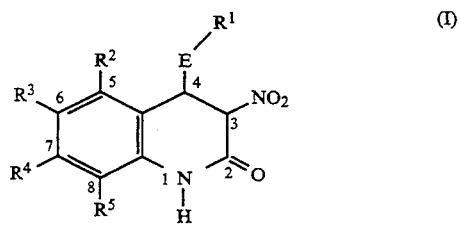

wherein

E represents a bond or a straight or branched alkylene chain containing from 1 to 4 carbon atoms;

$R^1$ represents hydrogen, —$OR^a$, —$NR^aR^b$, —$CO_2R^a$, —$CONR^aR^b$ or a group of formula

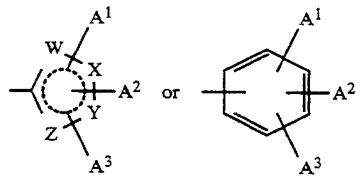

in which the broken circle represents two non-adjacent double bonds in any position in the five-membered ring;

W, X, Y and Z independently represent oxygen, sulphur, nitrogen or carbon, provided that no more than one of W, X, Y and Z represents oxygen or sulphur, at least one of W, X, Y and Z represents carbon and at least one of W, X, Y and Z is other than carbon;

$A^1$, $A^2$ and $A^3$ represent one, two or three substituents (not exceeding the maximum number permissible by the disposition of heteroatoms in the 5-membered ring), which substituents are independently selected from hydrogen, hydrocarbon, which is selected from $C_{1-6}$ alkyl, $C_{2-6}$ alkenyl, $C_{2-6}$ alkynyl, $C_{3-7}$ cycloalkyl, $C_{3-7}$ cycloalkyl ($C_{1-6}$) alkyl, aryl, selected from phenyl or naphthyl, or aryl ($C_{1-6}$) alkyl; a heterocyclic group selected from $C_{3-7}$ heterocycloalkyl, $C_{3-7}$ heterocycloalkyl ($C_{1-6}$) alkyl, heteroaryl and heteroaryl ($C_{1-6}$) alkyl groups, wherein said heterocycloalkyl groups are selected from piperidyl, poperazinyl and morpholinyl, and said heteroaryl groups are selected from pyridyl, quinolyl, isoquinolyl, pyridazinyl, pyrimidinyl, pyrazinyl, pyranyl, furyl, benzofuryl, thienyl, benz-thienyl, pyrrolyl, indolyl, imidazolyl, and oxadiazolyl groups; which groups can be substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, $C_{1-6}$ alkoxy ($C_{1-6}$) alkoxy, aryloxy, keto, $C_{1-3}$ alkylene-dioxy, nitro, cyano, carboxy, $C_{2-6}$ alkoxycarbonyl, $C_{2-6}$ aloxycarbonyl ($C_{1-6}$ alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkyl-sulphinyl, $C_{1-6}$ alkylsulphonyl, arylthio, amino, mono- or di ($C_{1-6}$) alkylamino, $C_{2-6}$ alkylcarbonylamino, $C_{2-6}$ alkoxycarbonylamino and $C_{2-6}$ alkoxycarbonylamino ($C_{1-6}$) alkyl; halogen, cayno, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, or —$CONR^aR^b$; or $A^1$ and $A^2$ or $A^2$ and $A^3$ together can represent an aryl or heteroaryl ring as defined above;

$R^2$, $R^3$, and $R^5$ independently represent hydrogen, hydrocarbon, as defined above, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and R4 is chloro; and $R^a$ and $R^b$ independently represent hydrogen, hydrocarbon or a heterocyclic group, as defined above.

2. A compound as claimed in claim 1 represented by formula IIA, and salts and prodrugs thereof:

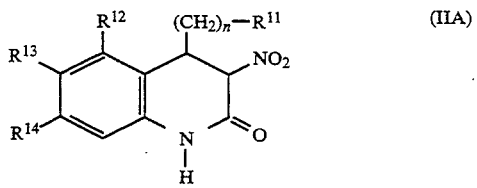

wherein n is zero, 1, 2 or 3;

$R^{11}$ represents hydrogen, —$OR^{16}$, —$NR^{16}R^{17}$, —$CO_2R^{16}$ or —$CONR^{16}R^{17}$;

$R^{12}$, $R^{13}$ and $R^{14}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl; and $R^{16}$ and $R^{17}$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl or heteroaryl($C_{1-6}$)alkyl, any of which groups may be optionally substituted.

3. A compound as claimed in claim 2 wherein n is zero and $R^{11}$ is hydrogen.

4. A compound as claimed in claim 2 wherein n is 1 and $R^{11}$ is methoxy, dimethylamino, methoxycarbonyl, ethoxycarbonyl, methylaminocarbonyl, phenylaminocarbonyl, benzylaminocarbonyl, dimethylaminocarbonyl or N-methyl-Nphenylaminocarbonyl.

5. A compound as claimed in claim 1 represented by formula IIB, and salts and prodrugs thereof:

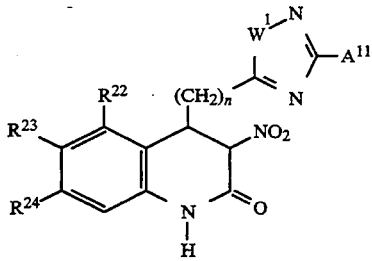

(IIB)

wherein n is zero, 1, 2 or 3;

$W^1$ represents oxygen or sulphur;

$A^{11}$ represents hydrogen, halogen, cyano, trifluoromethyl, nitro, hydroxy, amino, carboxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{1-6}$ alkoxy, $C_{2-6}$ alkenyloxy, $C_{1-6}$ alkylthio, $C_{2-6}$ alkenylthio, $C_{2-6}$ alkylcarbonyl, arylcarbonyl or $C_{2-6}$ alkoxycarbonyl; and $R^{22}$, $R^{23}$ independently represent hydrogen, halogen, cyano, trifluoromethyl, nitro, hydroxy, amino, carboxy, $C_{1-6}$ alkyl, $C_{1-6}$ alkoxy, $C_{1-6}$ alkylthio or $C_{2-6}$ alkoxycarbonyl.

6. A compound as claimed in claim 5 wherein n is 1, $W^1$ is oxygen and $A^{11}$ is methyl.

7. A compound as claimed in claim 1 selected from:
7-chloro-3-nitro-2-oxo-1,2,3,4-tetrahydroquinoline;
7-chloro-4-methoxycarbonylmethyl-3-nitro-2-oxo-1,2,3,4-tetrahydroquinoline;
7-chloro-4-ethoxycarbonylmethyl-3-nitro-2-oxo-1,2,3,4-tetrahydroquinoline;
7-chloro-4-methylaminocarbonylmethyl-3-nitro-2-oxo-1,2,3,4-tetrahydroquinoline;
7-chloro-3-nitro-2-oxo-4-phenylaminocarbonylmethyl-1,2,3,4-tetrahydroquinoline;
4-benzylaminocarbonylmethyl-7-chloro-3-nitro-2-oxo-1,2,3,4-tetrahydroquinoline;
7-chloro-4-(N,N-dimethylaminocarbonylmethyl)-3-nitro-2-oxo-1,2,3,4-tetrahydroquinoline;
7-chloro-4-(N-methyl-N-phenylaminocarbonylmethyl)-3-nitro-2-oxo-1,2,3,4-tetrahydroquinoline;
7-chloro-4-(3-methyl-1,2,4-oxadiazol-5-ylmethyl)-3-nitro-2-oxo-1,2,3,4-tetrahydroquinoline;
and salts and prodrugs thereof.

8. A pharmaceutical composition comprising a compound as claimed in claim 1 in association with a pharmaceutically acceptable carrier or excipient.

9. A method for the treatment of epilepsy or convulsions which require the administration of a selective non-competitive antagonist of NMDA receptors, which comprises administering to a patient in need of such treatment an effective amount of a compound of formula I as defined in claim 1 or a pharmaceutically acceptable salt thereof or a prodrug thereof.

* * * * *